United States Patent
Kobori et al.

(10) Patent No.: US 6,749,731 B2
(45) Date of Patent: Jun. 15, 2004

(54) GENE DETECTION CHIP AND DETECTION DEVICE

(75) Inventors: Shinichi Kobori, Tokyo (JP); Kazuhiro Nakama, Nagoshima (JP); Shingo Satoh, Nagoshima (JP); Hiroyoshi Miyahara, Chiba (JP)

(73) Assignees: Kyocera Corporation, Kyoto (JP); Tum Gene, Inc., Chiba (JP)

( * ) Notice: Subject to any disclaimer, the term of this patent is extended or adjusted under 35 U.S.C. 154(b) by 0 days.

(21) Appl. No.: 10/059,073

(22) Filed: Jan. 30, 2002

(65) Prior Publication Data

US 2002/0137083 A1 Sep. 26, 2002

(30) Foreign Application Priority Data

Jan. 31, 2001 (JP) ........................................ 2001-024750

(51) Int. Cl.$^7$ .......................... G01N 27/327; C12M 1/42
(52) U.S. Cl. ............... 204/403.01; 204/416; 204/286.1; 435/285.2
(58) Field of Search ........................ 204/403.01, 403.03, 204/416, 280, 286.1, 290.1; 435/461, 285.2

(56) References Cited

U.S. PATENT DOCUMENTS

| | | | |
|---|---|---|---|
| 4,840,893 A | | 6/1989 | Hill et al. |
| 5,457,041 A | * | 10/1995 | Ginaven et al. ............. 435/455 |
| 6,048,692 A | * | 4/2000 | Maracas et al. ................ 435/6 |
| 6,146,510 A | * | 11/2000 | Leader et al. ........... 204/403.01 |
| 6,368,851 B1 | * | 4/2002 | Baumann et al. ........ 435/285.2 |

FOREIGN PATENT DOCUMENTS

JP        09-288085       11/1997

OTHER PUBLICATIONS

CAPLUS abstract of Yelton ("Teflon–new resin with unusual properties," Plastics & Resins (1946), 5(No. 5), 14–16, 36).*
CAPLUS abstract of Bhansali et al. ("Resolving chemical/bio–compatibility issues in microfluidc MEMS sysems," Proceedings of SPIE—The International Society for Optical Engineering (1999), 3877 9Microfluidic Devices and Systems II), 101–109).*
Downs, Mark, et al., "New DNA Technology and the DNA Biosensor," Analytical Letters, vol. 20 (12), pp. 1897–1927 (1987).
Hashimoto, Koji, et al., "DNA sensor for electrochemical gene detection," Preparing for Clinical Care Analyses in the 21st Century, 16th International Symposium, 1996.
Molinier–Jumel, Catherine, et al., "Electrochemical Study of DNA–Anthracyclines Interaction," Biochemical and Biophysical Research Communications, vol. 84, No. 2, pp. 441–449 (1978).
Palecek, Emil, "Adsorptive Transfer Stripping Voltammetry: Determination of Nanogram Quantities of DNA Immobilized at the Electrode Surface," Analytical Biochemistry vol. 170, pp. 421–431 (1988).

(List continued on next page.)

*Primary Examiner*—T. Tung
*Assistant Examiner*—Alex Noguerola
(74) *Attorney, Agent, or Firm*—Covington & Burling

(57) ABSTRACT

A detection chip capable of detecting large amounts of genes with high sensitivity is provided.

The gene detection chip comprises a plurality of pins 12 as measurement electrodes, a common electrode 22 as a counter electrode therefor, and a tabular member 14 with a plurality of pin holes 15 for accommodating the pins. An arrangement may be adopted in which the diameters of the pin holes 15 taper off in the direction in which the pins are inserted, and the pins are held in place in the narrowest sections of the pin holes 15.

25 Claims, 10 Drawing Sheets

OTHER PUBLICATIONS

Takenaka, Shigeori, et al., "Bis–9–acridinyl Derivative Containing a Viologen Linker Chain: Electrochemically Active Intercalator for Reversible Labelling of DNA," J. Chem. Soc., Chem. Commun., vol. 21, pp. 1485–1487 (1990).

Takenaka, Shigeori, et al., "DNA Sensing on a DNA Probe-Modified Electrode Using Ferrocenylnaphthalene Diimide as the Electrochemically Active Ligand," Anal. Chem. vol. 72, pp. 1334–1341 (2000).

Takenaka, Shigeori, et al., "Electrochemically active threading intercalator with high stranded DNA selectivity," J. Chem. Soc., Chem. Commun., No. 10, pp. 1111–1112 (1998).

Takenaka, Shigeori, "Synthetic threading intercalators as a new analytical probe for nucleic acid and gene detection," Business Kagaku, vol. 48, No. 12, pp. 1095–1105 (1999).

Takenaka, Shigeori, et al., "Threading Intercalators as a New DNA Structural Probe," Bull. Chem. Soc. Jpn, vol. 72, pp. 327–337 (1999).

Yamashita, Kenichi, et al., "Electrochemical Detection of Base Pair Mutation," Chemistry Letters, pp. 1038–1039 (2000).

Ihara, Toshihiro et al., "Synthesizing and Applying the Bis–Inercalator as an Electrochemical Detection Probe of DNA," Proceedings of the Japan Society for Analytical Chemistry, p. 54 (1989).

Takanaga, Shigeori et al., "Synthesizing the Electrochemical Threading Type Intercalator and Applying the Electrochemical Threading Type Intercalator to a DNA Sensor," Proceedings of the Japan Society for Analytical Chemistry, pp. 137–138 (1996).

* cited by examiner

GENE DETECTION CHIP AND DETECTION DEVICE

TECHNICAL FIELD

The present invention relates to a gene detection chip and detection device capable of detecting and analyzing gene base sequences as well as gene abnormalities such as genetic DNA single base substitution SNPs (single nucleotide polymorphisms: mutations of human genetic code), multiple base substitutions, point mutations, and genetic defects.

BACKGROUND ART

Methods in which probe DNA is immobilized on an electrode, the probe DNA is hybridized with sample DNA, and the resulting hybrid is electrochemically detected have been proposed as a means of detecting the base sequence of gene DNA (see Japanese Patent Laid-open No. 9-288080 and Proceedings of the 57th Meeting of the Japan Society of Analytical Chemistry, pp. 137–138, 1996) These methods allow such hybrids to be detected with high sensitivity.

There exist, however, enormous numbers of such single base genetic substitution SNPs, genetic mutations, and the like, so at least 2,000,000 single base genetic substitution SNPs must be identified in order, for example, to map such single base substitution SNPs with a density (resolution) of 15 kB in humans. Genetic point mutations related to existing disorders also exist in large numbers. A means that can be used to comprehensively analyze such single base substitutions or point mutations.

The present invention, which was perfected in view of this situation, provides a gene detection chip and detection device that allow large amounts of genes to be detected (that is, processed with a high throughput) and allow detection and analysis procedures to be carried out with high sensitivity.

BRIEF SUMMARY OF THE INVENTION

The gene detection device of the present invention comprises a plurality of pins that constitute measurement electrodes, and a common electrode that constitutes a counter electrode for these measurement electrodes. At least portions of the surfaces of the abovementioned pins are coated with a resin. Here, a so-called detection chip is included in the meaning of the term "detection device". Furthermore, a device constructed by attaching a detection chip to a measuring device is also included in the meaning of the term "detection device".

In the above arrangement, the pins may be configured such that the resin is applied only to part of the surface on which the Au film is formed. Covering only part of the outermost surface of the pins with resin makes it possible to immobilize a gene solely on the uncoated, exposed portions and allows the exposed surface area to be kept constant and the amount of immobilized probe to be controlled, producing detection results that have higher sensitivity. In addition, an arrangement in which the lateral surface of each pin is covered with resin and the gene is immobilized solely on the exposed portion (located at the end opposite from the base end of the pin fixedly supported on the supporting member) is preferred because the exposed surface area can be readily determined based on the thickness of the pin electrodes. The coating resin should be PEEK (polyether ether ketone), a fluororesin or other thermoplastic resin, or an epoxy resin because of considerations related to chemical resistance.

In the above, the abovementioned pins may contact the surface of a supporting member or may be implanted in the surface of a supporting member, and the lateral surfaces of these pins and the portions of the surface of the abovementioned supporting member that are not contacted by these pins or in which these pins are not implanted may be respectively coated with a resin. In this case, the abovementioned resin is preferably a fluororesin. In particular, a copolymer of tetrafluoroethylene and hexafluoropropylene is especially desirable.

In the above, the device may comprise a plate-form member which consists of a resin and which has a plurality of pin holes into which the abovementioned plurality of pins are respectively inserted, and portions of the surfaces of the abovementioned pins may be coated by this plate-form member.

According to the present invention, a plurality of pins can be secured easily and stably because the pins are inserted into and held in place inside the pin holes with the aid of a plate-form member provided with a plurality of pin holes at positions that match the pin positions.

Each pin can be tightly fitted into the corresponding pin hole when inserted thereinto as a result of the fact that the pin hole diameter is the same as or slightly smaller than the outside diameter of the pin. In other words, each pin can be held airtightly by the plate-form member, preventing the solutions used in the detection process from penetrating through the contact areas between the pins and pin holes.

The present invention provides a gene detection device characterized in that the diameters of the pin holes taper off in the direction in which the pins are inserted, and the pins are held in place in the narrowest sections of the pin holes. According to the present invention, the pin hole diameters vary in tapered fashion, and the pins are inserted from the side with the large diameter and are held in place in the section with the minimum hole diameter, thus facilitating positioning when the pins are inserted into the pin holes and making it easier to conduct operations in which the tabular member is mounted on the pins. Another feature is that because the minimum hole diameter is the same as or slightly less than the pin diameter, the pins are held airtightly by the plate-form member when the pins are inserted into the pin holes, and the solutions used in the detection process can be prevented from penetrating through the contact areas between the pins and pin holes.

It is desirable that the abovementioned pins contact the surface of the supporting member or be implanted in the surface of the supporting member, and that the abovementioned plate-form member adhere tightly to the surface of the abovementioned supporting member.

According to the present invention, the pins are held in place while the plate-form member is tightly bonded to the supporting member, making it possible to prevent the solutions used in the detection process from penetrating through the joint between the plate-form member and the supporting member. The supporting member may also be a circuit substrate whose interior contains electric circuitry.

The plate-form member should preferably contain a thermoplastic resin as the principal component thereof. Specifically, PTFE (polytetrafluoroethylene) and other fluororesins can be cited as examples of suitable materials, as can PEEK (polyether ether ketone). Using a plate-form member composed of a thermoplastic resin makes it possible to provide a gene detection chip that has excellent heat resistance and is highly resistant to the chemicals (alkalis, acids, and the like) used for detection pretreatments. Such enhanced chemical and heat resistance makes this material suitable for processes in which a detection cycle is followed by the removal of sample DNA and the re-hybridization of another sample DNA to allow the gene detection chip to be reused, or for processes in which a probe gene is removed and another probe gene is re-immobilized on the pins to allow the gene detection chip to be reused.

It is also possible to fabricate the present detection device by a process in which the heat-shrinkage properties of a thermoplastic resin (for example, PEEK) are utilized to form a tabular member whose pin holes have somewhat enlarged diameters, pins are inserted into the pin holes, the plate-form member is heat-treated to induce heat shrinkage, and the diameters of the pin holes are reduced to cause the pin holes to constrict the pins. Adopting this arrangement facilitates positioning when pins are inserted into the pin holes because the diameters of the pin holes are greater than the outside diameters of the pins, makes it easier to mount the plate-form member on the pins, and allows the pins to be held airtightly in a state in which the pins and the pin holes are tightly joined with each other.

A particularly preferred feature of the present invention is that the plate-form member be composed of PTFE (polytetrafluoroethylene). PTFE is highly flexible and can be used to airtightly hold the pins in the pin holes. In addition, the high flexibility of PTFE makes this resin suitable for creating a tight bond between the plate-form member and the ceramic supporting member.

A particularly preferred feature of the present invention is that the pins consists of an Au (gold) film on the surface of an alloy primarily containing Fe (iron), Ni (nickel), and Co (cobalt).

Using pins in which an Au film is formed on the surface of an Fe—Ni—Co alloy is preferred from the standpoint of mass production. Such an allow is preferred because it has a coefficient of linear expansion of between $5.0 \times 10^{-6}/°$ C. and $9.0 \times 10^{-6}/°$ C., and can easily conform to the expansion of a ceramic material. An alloy having such a coefficient of linear expansion may, for example, be obtained by adding 15–20 wt % of an Ni component, 25–30 wt % of a Co component, and 50–60 wt % of an Fe component. The alloy may also contain no more than 1.0 wt % of impurities.

The thickness of the Au film should preferably be kept 20 $\mu$m or less to achieve good coverage of the substrate and to prevent cost overruns due to the formation of an excessively thick film. The Au film should preferably be an Au plating formed by conventional electroplating. It is also possible to perform Ni plating as a surface preparation treatment that precedes Au plating, and to subsequently form an Au plating thereon.

Because the present invention features the above-described pins, genes can be electrochemically detected with high sensitivity.

Using an array of pins allows a plurality of genes to be analyzed at the same time. As used herein, the term "array" refers to a large number of pins arranged such that they extend parallel to each other from a specific surface.

The gene detection device of the present invention comprises a supporting member for fixedly supporting one end of each pin, with the supporting member primarily composed of a ceramic. The supporting member contains a ceramic as its principal component, and hence has excellent chemical resistance and strength. The ceramic should preferably be alumina ($Al_2O_3$), silicon carbide (SiC), silicon nitride ($Si_3N_4$), zirconia ($ZrO_2$), beryllia, or the like because of considerations related to chemical resistance. Alumina is particularly suitable. The ceramic should preferably have a coefficient of linear expansion of between $6.0 \times 10^{-6}/°$ C. and $11.0 \times 10^{-6}/°$ C. to facilitate joining with the pins. The supporting member should preferably contain at least 90 wt % of the ceramic.

In the above arrangement, a plurality of PCR products having identical or different gene sequences, such oligonucleotides, mRNA, cDNA, PNA (peptidic nucleic acid), and LNA (Locked Nucleic Acids from Proligo LLC), may be immobilized on the pins.

The above-described gene detection device may, for example, be used to detect gene base sequences, single base substitution SNPs, multiple base substitutions, point mutations, translocations, defects, amplifications, and triplet repeats. The presence or absence of genes related to monogenic disorders (such as muscular dystrophy, hemophilia, and phenyl ketonuria) and multifactorial genetic diseases (such as diabetes, cancer, hypertension, myocardial infarction, and obesity) can be diagnosed, or premorbid genes can be diagnosed by genetic screening based on the use of the inventive detection chip, which can thus be employed as a diagnostic material for selecting an appropriate treatment or drug.

Furthermore, the present invention provides a gene detection chip which comprises a plurality of pins that constitute measurement electrodes, and in which at least portions of the surfaces of the abovementioned pins are coated with a resin. This gene detection chip may also be a chip which has a common electrode that constitutes a counter electrode for the abovementioned plurality of pins. Specifically, the detection chip of the present invention may be a chip which has both pin electrodes and a common electrode, or may be a chip which has only pin electrodes with no common electrode, and in which measurements are performed by attaching the detection chip to a solution tank that is equipped with a common electrode.

The abovementioned pins may contact the surface of the supporting member or be implanted in the surface of the supporting member, and the lateral surfaces of the abovementioned pins and the portions of the surface of the supporting member that are not contacted by these pins or in which these pins are not implanted may be respectively coated with a resin.

Furthermore, the device may comprise a plate-form member which consists of a resin and which has a plurality of pin holes into which the abovementioned plurality of pins are respectively inserted, and portions of the surfaces of the abovementioned pins may be coated by this plate-form member.

Furthermore, the abovementioned pins may be pins in which an Au film is formed on the surface of an alloy whose main components are Fe, Ni and Co. The present invention also provides the above-described gene detection chip and a measurement device capable of accepting or releasing this detection chip.

The present invention provides a gene detection chip which comprises a plurality of pins that constitute measurement electrodes, and a common electrode that constitutes a counter electrode for these measurement electrodes, and in which the abovementioned pins are formed by forming an Au film on the surface of an alloy whose main components are Fe, Ni and Co.

It is desirable that the abovementioned pins contact the surface of the supporting member or be implanted in the surface of the supporting member, and that the abovementioned supporting member be constructed with a ceramic as the main component of this supporting member.

It is desirable that the abovementioned pins contact the surface of the supporting member or be implanted in the surface of the supporting member, and that the abovementioned supporting member be constructed with alumina as the main component of this supporting member.

Large amounts of genes can thus be concurrently detected through simple operations with extremely high sensitivity by employing the above-described chip to allow electrochemically active molecules to bind following hybridization or to perform hybridization in the presence of electrochemically active molecules.

BRIEF DESCRIPTION OF THE DRAWINGS

FIG. 1 is a diagram depicting the gene detection chip pertaining to a first embodiment of the present invention, wherein

(1: main body, 2: frame, 10: detection chip, 11: base plate, 12: pin, 13: coating resin, 14: tabular member, 15: pin hole, 16: distal end of pin, 17: base end of pin, 18: pin hole, 22: common electrode)

DESCRIPTION OF THE PREFERRED EMBODIMENTS

Embodiments of the gene detection chip and detection device pertaining to the present invention will now be described with reference to the accompanying drawings. The drawings are used merely to illustrate the embodiments of the present invention and are nonlimiting in nature.

(Detection Chip Pertaining to First Embodiment)

Figure 1A:
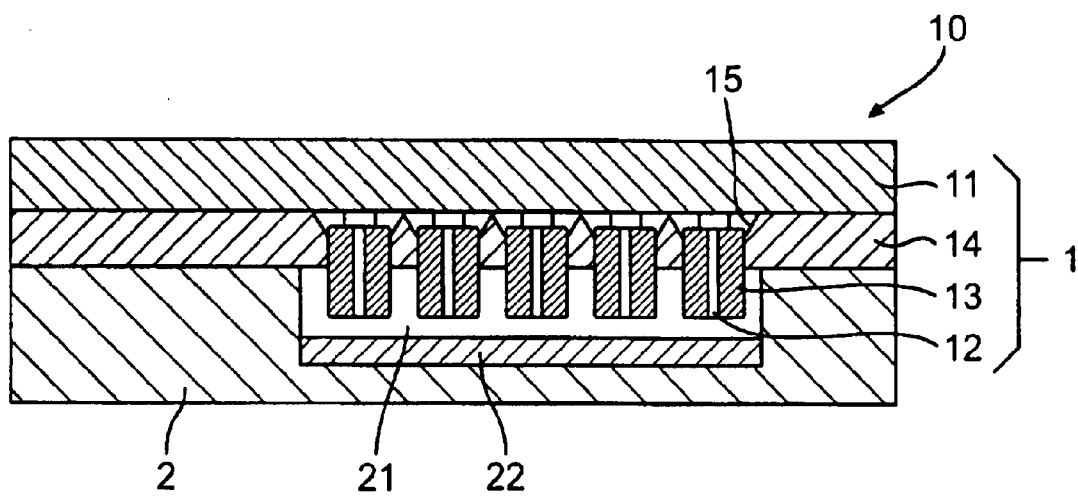
FIG. 1(a) is a partial fragmentary view thereof.
Figure 1B:
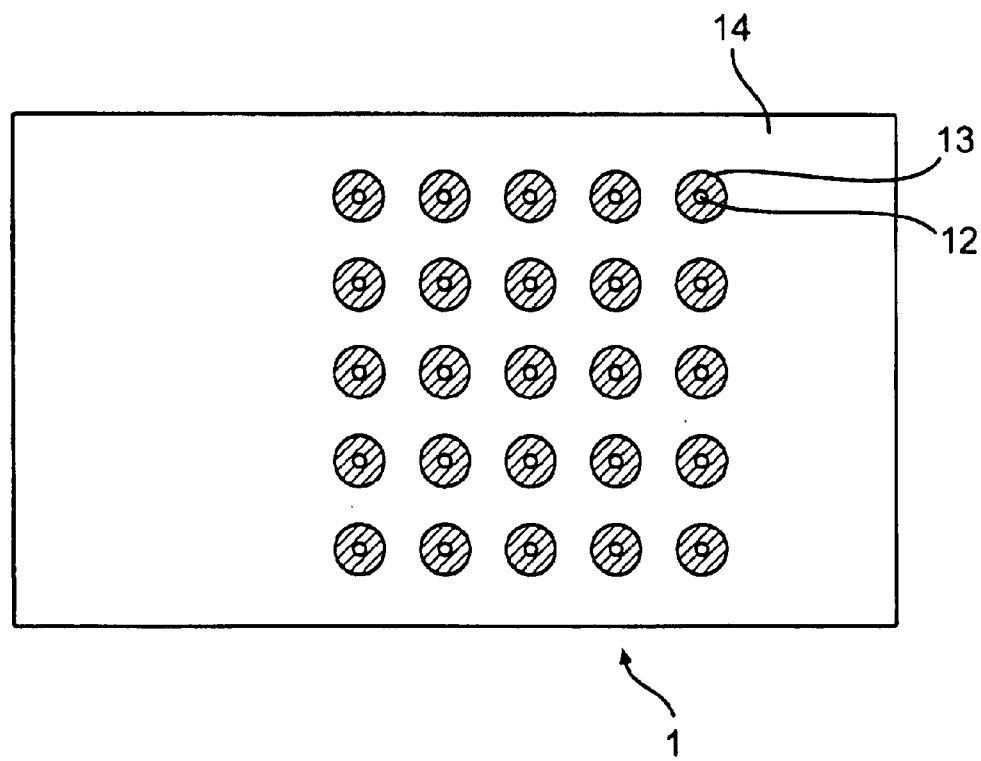
FIG. 1(b) is a diagram depicting the main body viewed from the pin mounting side.
Figure 2:
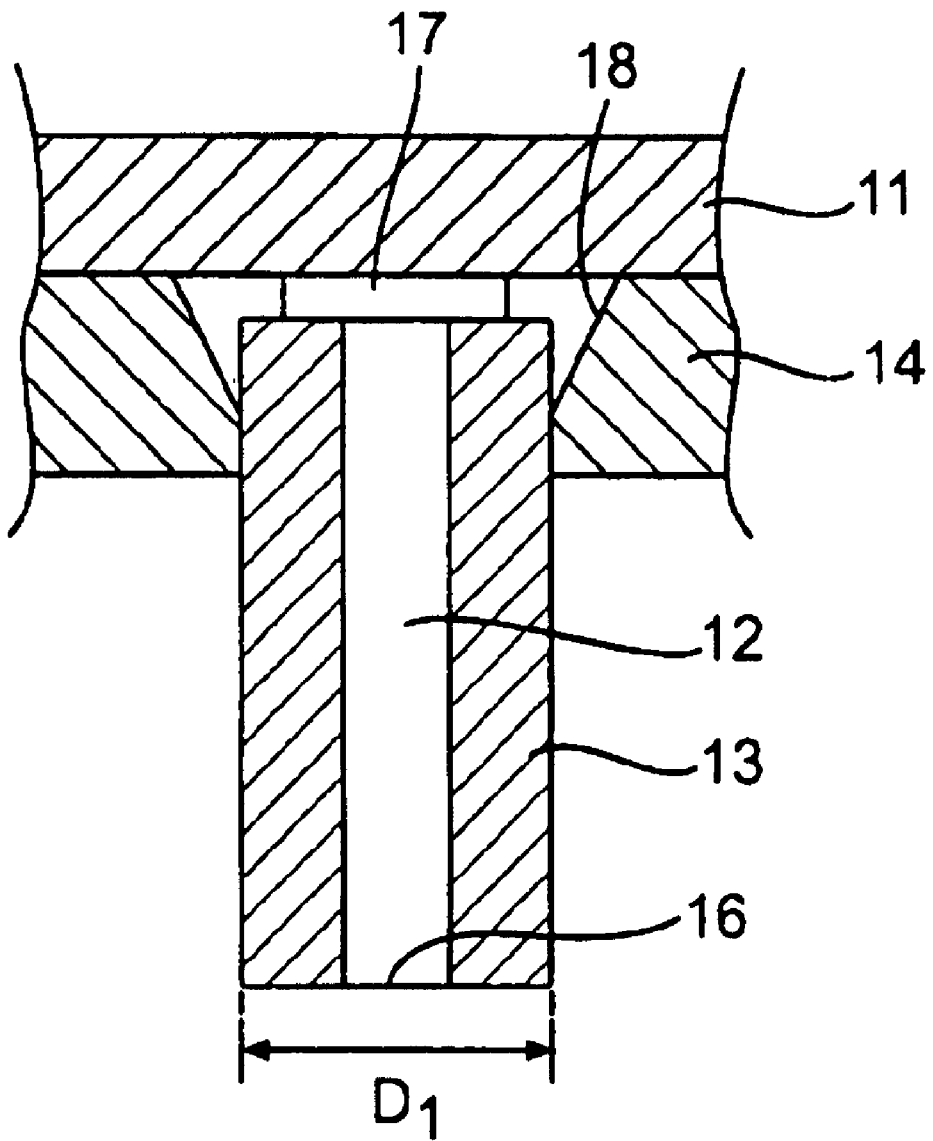
FIG. 2 is a fragmentary magnified view of FIG. 1(a)

FIG. 1 is a diagram depicting the gene detection chip pertaining to a first embodiment of the present invention, wherein FIG. 1(a) is a partial fragmentary view thereof, and FIG. 1(b) is a diagram depicting the main body viewed from the pin mounting side. FIG. 2 depicts the relation between a pin, a base plate, and a tabular member and represents a fragmentary magnified view of FIG. 1(a).

The gene detection chip 10 is configured as a card or cassette chip and is composed of a main body 1 and a frame 2 detachably mounted thereon, as shown in FIGS. 1(a) and 1(b).

The main body 1 comprises a base plate 11, a plurality of pins 12 fixedly supported (preferably by wax) on one surface of the base plate 11, a coating resin 13 for covering the lateral surfaces of the pins 12, and a tabular member 14 provided with pin holes 15 for inserting the pins 12.

The plurality of pins 12 are uniformly arranged parallel to each other as an array of pins extending from one side of the base plate 11, as shown in FIG. 1(b). The base plate 11 accommodates an electric circuit, and the plurality of pins 12 (measurement electrodes) are connected independently from each other to the wires of the electric circuit. The other ends of the wires are connected to pin terminals and a common electrode terminal. It is possible to adopt an arrangement in which the wires connected to the pins are connected one by one to the corresponding pins, and are thus connected to individual pin terminals. An alternative is a structure in which the pins and conductors of individual matrix wires are connected via FETs (field-effect transistors) at the intersections of a wiring matrix composed of large numbers of longitudinal and transverse wires, as is the case with the matrix electrodes of an active-matrix TFT liquid-crystal display or other device provided with TFT switching elements. Adopting such a structure makes it possible to scan the wires of the wiring matrix, to switch on the selected TFT, and to electrically connect a specific pin to the terminal.

The base end 17 of a pin 12 is fixedly supported on the base plate 11, as shown in FIG. 2. The lateral surface of the pin 12 is covered by the coating resin 13. The coating resin should preferably be PTFE (polytetrafluoroethylene) or epoxy resin. The pin covered by the coating resin 13 is inserted into a pin hole 18 provided with a tapered surface such that the pin hole diameter varies in tapered fashion. The minimum diameter of the pin hole 18 is slightly less than the outside diameter D1 or the pin covered by the coating resin 13, and inserting the pin 12 into the pin hole 18 causes the section with the minimum hole diameter to be subjected to pressure from the coated lateral surface of the pin 12. The coated pin 12 is thus airtightly fitted into the pin hole 18. The tabular member 14 is fixedly bonded to the base plate 11.

Adopting the above-described arrangement makes it possible to prevent the solution in a depression 21 from penetrating between the coating resin 13 and the tabular member 14 or between the tabular member 14 and the base plate 11.

The pins 12 are composed of an alloy primarily containing Fe, Ni, or Co, and the surfaces thereof are plated with Au. The alloy should preferably contain 15–20 wt % of an Ni component, 25–30 wt % of a Co component, and 50–60 wt % of an Fe component.

The distal end 16 of each pin is left exposed without being covered by the coating resin 13, and an SH-modified oligonucleotide (PCR product) obtained by modifying an oligonucleotide with thiol and introducing SH groups into the 5' end thereof is immobilized on the exposed area. The SH-modified oligonucleotide has a length that includes 20–50 bases and is immobilized via the SH groups on the Au-free area. To immobilize the SH-modified oligonucleotide, each pin is modified with the same or different type of DNA by the introduction of the pins 12 into the DNA compartments of a microplate whose compartments are arranged at the same pitch as the pins 12. Techniques to immobilize an SH-modified oligonucleotide on Au by means of SH groups are well known.

SH-Au bonding and pretreatment methods that precede the Au plating of pin electrode surfaces are described, for example, by C. D. Bain in *J. Am. Chem. Soc.* (No. 111, p. 321, 1989) and by J. J. Gooding in *Anal Chem.* (No. 70, p. 2396, 1998). Probe genes can, for example, be removed by the method described by C. D. Bain in *J. Am. Chem. Soc.* (No. 111, p. 321, 1989).

The tabular member 14 should preferably contain PTFE as the principal component thereof.

The base plate 11 should preferably contain alumina as the principal component thereof.

A depression 21 capable of accepting a solution (sample DNA, threading intercalator, washing solution, or the like) is provided to the frame 2 at a location that matches that of the pins 12. The frame 2 may be composed of a ceramic, resin, or the like.

A common electrode 22 is mounted in the depression 21, and the common electrode 22 is connected to a common electrode terminal (not shown). The common electrode 22 is located along part (for example, the periphery) or all of the bottom of the depression 21, on the inner peripheral surface near the bottom of the depression 21, or in another area not in contact with the pins. A seal may be provided along the periphery of the depression 21.

The frame 2 can be detachably bonded to the main body 1 by means of a structure in which, for example, irregularities (not shown) elastically fittable into each other are provided to the contact surfaces of the main body and the frame. It is also possible to secure the main body 1 and the frame 2 with clips or clamps or to hold the components together by an electromagnet.

Measurements are taken to detect the electric current flowing between the common electrode and the pins when voltage is applied between the common electrode terminal and each pin electrode terminal. The detection is performed using a liquid electrolyte containing electrochemically active molecules, as described in detail in Japanese Patent Laid-open No. 9-288080.

Genes can be rapidly detected with high sensitivity with the aid of the detection chip described above.

Detection Device Equipped With Detection Chip Pertaining to First Embodiment

Figure 3:
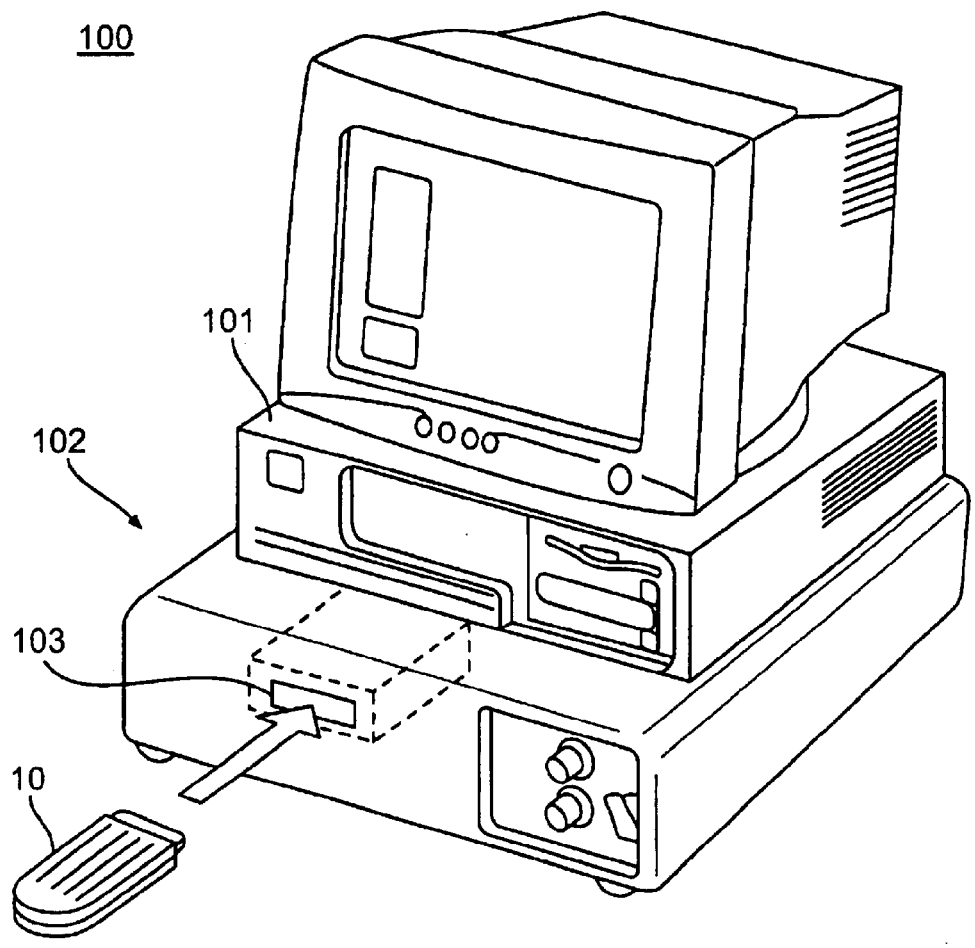
FIG. 3 is a perspective view depicting the overall structure of a detection device equipped with the detection chip pertaining to the first embodiment of the present invention.

FIG. 3 is a perspective view depicting the overall structure of a detection device equipped with the detection chip pertaining to the first embodiment.

In FIG. 3, the gene detection device 100 pertaining to the present invention comprises a detection chip 10, a measurement device 102 having an insertion slot 103 capable of accommodating the detection chip 10, and a personal computer 101.

The probe gene is immobilized on the distal ends 16 of the pins 12, and the depression 21 is then filled with a solution containing the target gene. A detection chip 10 comprising a frame 2 mounted on the main body 1 is subsequently introduced into the insertion slot 103, the temperature is set to the hybridization level with the aid of a temperature controller composed of a Peltier element mounted inside the measurement device 102, and the probe gene and target gene are hybridized. The detection chip 10 is taken out of the measurement device 102, the interior of the depression 21 is rinsed, an intercalator is introduced into the double strand obtained by hybridization, and the detection chip 10 is introduced into the insertion slot 103. The common electrode terminal and the pin terminals are connected at this time to the corresponding terminals inside the measurement device 102. Weak current flows via the common electrode between the pins 12 and the double strand obtained by hybridization when voltage is applied to the common electrode 22 and the pins 12. The target He gene can be detected by controlling the temperature with the Peltier element mounted inside the measurement device 102 and measuring the value of the electric current at various temperatures.

(Detection Chip Pertaining to Second Embodiment)

Figure 4:
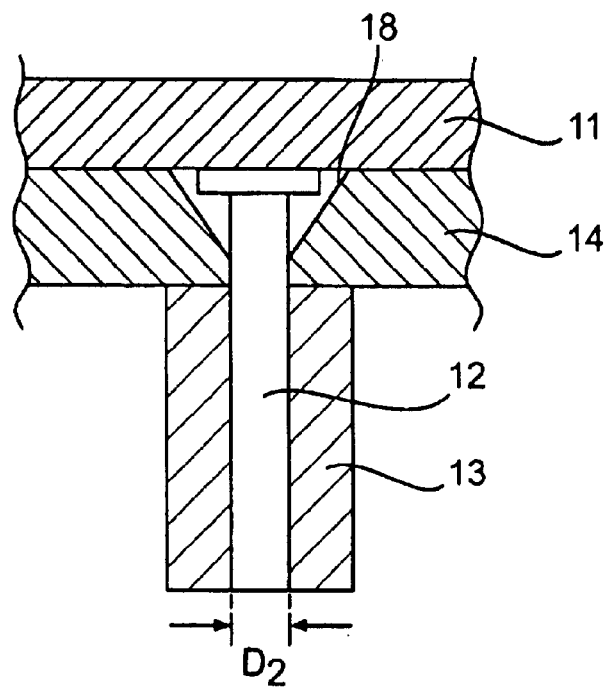
FIG. 4 is a cross-sectional magnified view depicting the gene detection chip pertaining to a second embodiment of the present invention.

FIG. 4 is a cross-sectional magnified view of the relation between the pins, base plate, and tabular member of the gene detection chip pertaining to a second embodiment of the present invention.

The only difference between the present embodiment and the above-described first embodiment is that the base ends of the pins 12 are held in place inside the pin holes 18.

Specifically, the pins 12 are inserted into the pin holes 18 formed in the tabular member, as shown in FIG. 4. The pin holes 18 have tapered surfaces, the minimum diameter thereof is slightly less than the outside diameter D2 of the pins, and the pins 12 are inserted into the pin holes 18 of the tabular member 14, whereby the sections with the minimum hole diameter are subjected to pressure from the lateral surfaces of the pins 12, allowing the pins to form an airtight fit. According to the present embodiment, a tabular member 14 is provided, and a coating resin 13 is then applied to the lateral surfaces of pins 12 in the areas that extend from the tabular member 14. The tabular member 14 is composed of PTFE and is tightly bonded to the base plate 11.

Adopting this arrangement makes it possible to prevent a solution from penetrating between the pins 12 and the tabular member 14 or between the tabular member 14 and the base plate 11.

Genes can be rapidly detected with high sensitivity with the aid of the detection chip described above.

(Detection Chip Pertaining to Third Embodiment)

Figure 5:
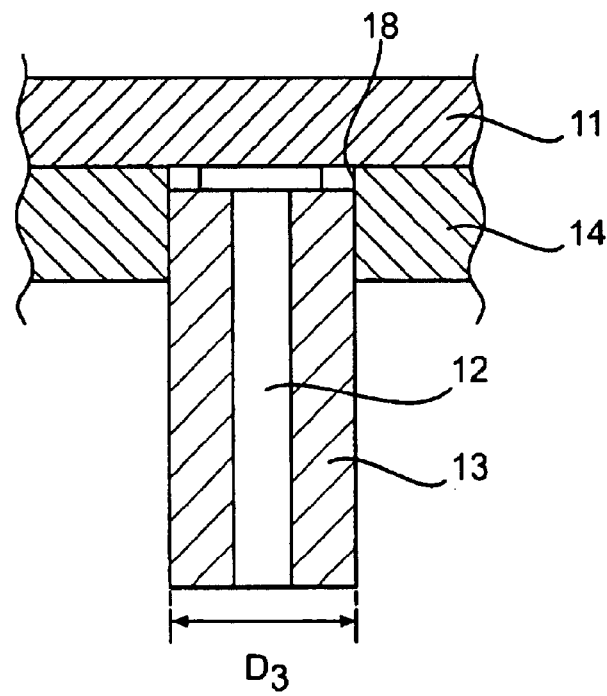
FIG. 5 is a cross-sectional magnified view depicting the gene detection chip pertaining to a third embodiment of the present invention.

FIG. 5 is a cross-sectional magnified view of the relation between the pins, base plate, and tabular member of the gene detection chip pertaining to a third embodiment of the present invention.

The only difference between the present embodiment and the above-described first embodiment is that the pin holes 18 in the tabular member 14 are devoid of the tapered surfaces.

Specifically, the pins 12 are inserted into the constant-diameter pin holes 18, as shown in FIG. 5. The diameter of the pin holes 18 is made equal to the outside diameter D3 of the pins covered by the coating resin 13, and the pin holes 18 and the coating resin 13 are pressed against each other by insertion, allowing the coated pins 12 to form an airtight fit with the pin holes 18. The tabular member 14 is composed of PTFE and is tightly bonded to the base plate 11, holding the pins in an airtight manner. Adopting this arrangement makes it possible to prevent a solution from penetrating between the coating resin 13 and the tabular member 14 or between the tabular member 14 and the base plate 11.

Genes can be rapidly detected with high sensitivity with the aid of the detection chip described above.

(Detection Chip Pertaining to Fourth Embodiment)

Figure 6:
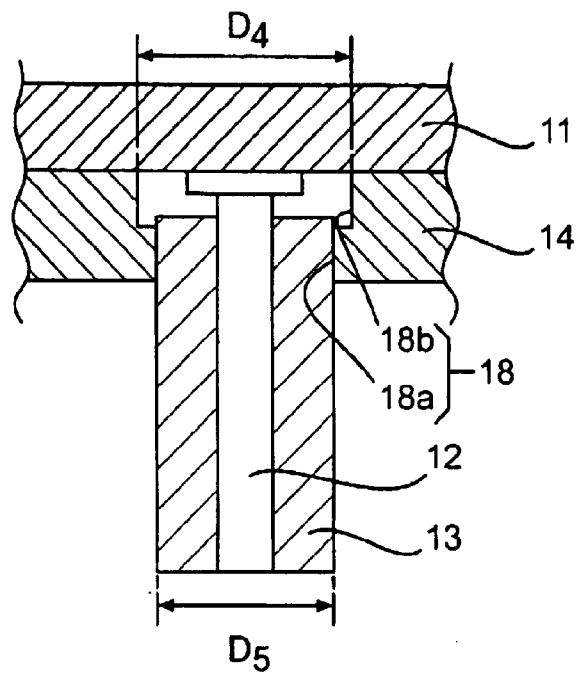
FIG. 6 is a cross-sectional magnified view depicting the gene detection chip pertaining to a fourth embodiment of the present invention.

FIG. 6 is a cross-sectional magnified view of the relation between the pins, base plate, and tabular member of the gene detection chip pertaining to a fourth embodiment of the present invention.

The only difference between the present embodiment and the above-described first embodiment is that the pin hole diameter of the tabular member 14 varies in a stepwise manner and the coating resin 13 on the base ends of the pins 12 is held in place inside pin holes 18a.

According to the present embodiment, a pin hole 18 of the tabular member 14 comprises a portion 18a with a hole diameter D5, and a portion 18b with a hole diameter D6, as shown in FIG. 6. The lateral surface of each pin 12 is covered by a coating resin 13 such that the coated pin has the outside diameter D5. Inserting the coated pin 12 into the pin hole 18 causes the coating resin 13 and the portion 18a with the hole diameter D5 to come into contact with each other, and the coated pin 12 to be held airtightly. The tabular member 14 is composed of PTFE and is tightly bonded to the base plate 11. Adopting this arrangement makes it possible to prevent a solution from penetrating between the coating resin 13 and the tabular member 14 or between the tabular member 14 and the base plate 11.

Genes can be rapidly detected with high sensitivity with the aid of the detection chip described above.

(Detection Chip Pertaining to Fifth Embodiment)

Figure 7:
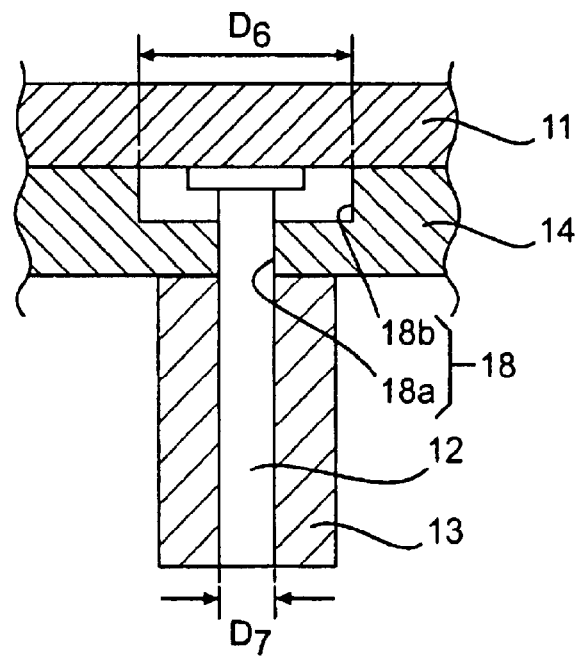
FIG. 7 is a cross-sectional magnified view depicting the gene detection chip pertaining to a fifth embodiment of the present invention.

FIG. 7 is a cross-sectional magnified view of the relation between the pins, base plate, and tabular member of the gene detection chip pertaining to a fifth embodiment of the present invention.

The only difference between the present embodiment and the above-described first embodiment is that the pin hole diameter of the tabular member 14 varies in a stepwise manner and the base ends of the pins 12 are modified such that they are held in place inside the pin holes 18a.

Specifically, a pin hole 18 of the tabular member 14 comprises a portion 18a with a hole diameter D7, and a portion 18b with a diameter D6. Inserting a pin 12 with the outside diameter D7 into a pin hole 18a of the tabular member 14 causes the lateral surface of the pin 12 to exert pressure on the pin hole 18a and causes the pin 12 to be held airtightly in the pin hole 18a. According to the present embodiment, the tabular member 14 is provided, and a coating resin 13 is then applied to the pins 12 in the areas that extend from the tabular member 14. The tabular member 14 is composed of PEEK (Polypenco® from Nippon Polypenco Limited) and is tightly bonded to the base plate 11. Adopting this arrangement makes it possible to prevent a solution from penetrating between the pins 12 and the tabular member 14 or between the tabular member 14 and the base plate 11.

Genes can be rapidly detected with high sensitivity with the aid of the detection chip described above.

The above-described detection chips of the second to fifth embodiments can be adapted to a detection device and used for detection in the same manner as the detection chip pertaining to the first embodiment.

The above description was merely an illustration of some of the embodiments of the present invention and does not impose any limitations on the alloy that constitutes the pins, the coating resin that covers the pins, or the components that constitute the base plate and the tabular member.

Although the above description was given with reference to cases in which a coating resin was applied to the outermost lateral surfaces of the pins, the coating areas are not limited to the lateral surfaces alone and may include any part of the outermost surfaces of the pins.

Although the above description was given with reference to cases in which one end of each pin was fixedly supported on the base plate, it is also possible to embed one end of each pin into the base plate. Although the above description was given with reference to cases in which 25 pins were provided, it is also possible to vary the number of pins as appropriate.

(Detection Chip of Sixth Embodiment)

Figure 8:
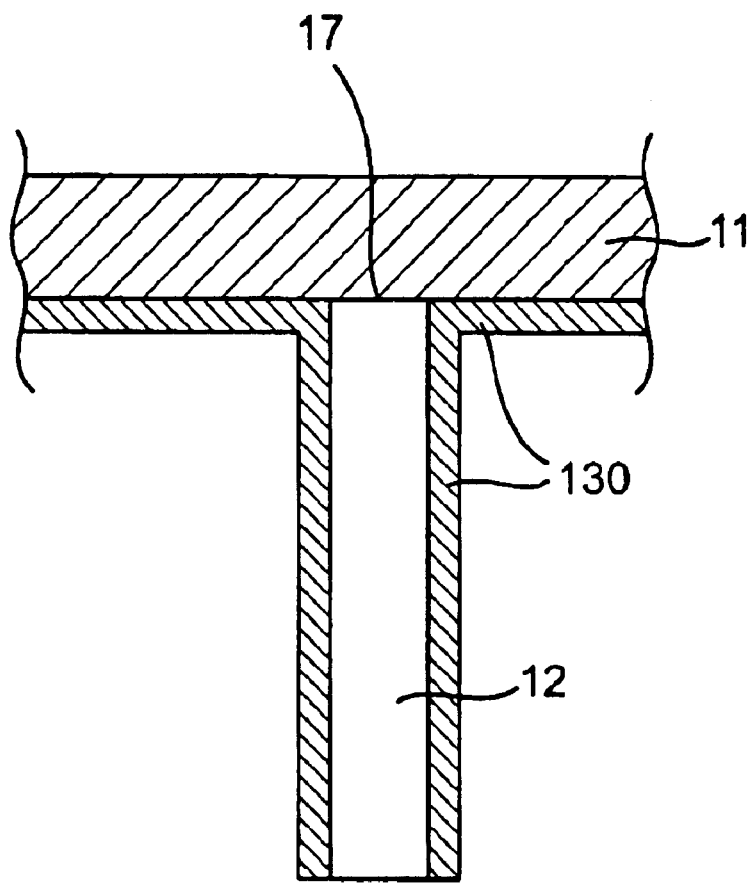
FIG. 8 is an enlarged sectional view of a gene detection chip constituting a sixth embodiment of the present invention.

FIG. 8 is an enlarged sectional view which shows the relationship of the pins, supporting member and coating parts of a gene detection chip constituting a sixth embodiment of the present invention.

The present embodiment differs from the abovementioned first embodiment in that the lateral surfaces of the pins 12 and the portions of the surfaces of the supporting member 11 to which the pins 12 are not fastened are respectively coated by a resin 130.

As is shown in FIG. 8, the base parts 17 of the pins 12 are supported by and fastened to the supporting member 11. It is desirable that this resin consist of a copolymer of tetrafluoroethylene and hexafluoropropylene.

As a result of the above, the entry of the solution into the supporting member 11 can be very effectively prevented.

EXAMPLES

Examples will be described below; however, it goes without saying that the present invention is not limited to these examples.

Example 1

(Sample 1)

In order to cause only the distal ends of Au-plated pins to act as electrodes, the lateral surface portions of the pins were coated with a polytetrafluoroethylene as Sixth Embodiment. The coating was performed by a publicly known spray coating method.

Next, only the distal end portions of the pins protruding from the substrate were immersed in 2M NaOH and subjected to a boiling treatment for 1 hour. Afterward, Sample 1 was obtained by immersing the pins in concentrated $HNO_3$ and performing a pretreatment for 0.5 hour.

(Sample 2)

The lateral surface portions of the pins were coated in the same manner as described above using an ethylene-copolymerized tetrafluoroethylene instead of a polytetrafluoroethylene; next, a pretreatment was performed, thus producing Sample 2.

(Sample 3)

The lateral surface portions of the pins were coated in the same manner as described above using a tetrafluoroethylene/hexafluoropropylene copolymer instead of a polytetrafluoroethylene; next, a pretreatment was performed, thus producing Sample 3.

(Visual Observation of Conditions of Deterioration)

The conditions of deterioration of the coating resin before and after pretreatment were visually observed for Samples 1 through 3 thus obtained. In this visual observation, almost no deterioration of the resin was seen in Sample 1 or Sample 3. In Sample 2, signs of a slight deterioration of the resin caused by the pretreatment were seen.

(Evaluation of Electrochemical Characteristics)

An evaluation of the electrochemical characteristics was performed for Samples 1 and 3. An ECA CHIP READER TGE 1000 (manufactured by TUM Gene, Inc.) was used to perform measurements, and DPV (differential pulse voltammetry) was performed using a three-pole system in which a Pt counter electrode and an Ag/AgCl reference electrode were installed. All measurements were performed at room temperature. In more concrete terms, the variation in the multi-electrode response was measured for Samples 1 and 3 by performing DPV in a 0.2M phosphate buffer (pH 7.0) containing 500 μM ferrocenecarboxylic acid, and the peak current value ipa of the ferrocenecarboxylic acid, DPV voltammogram waveform and the like were evaluated.

The pretreatment was repeated three times, and respective DPV measurements were made. Regarding Samples 1 and 3, the peak current value ipa (μA) of each pin (25 pins) is measured. The Mean Value was calculated, in which the Mean Value of the first measured ipa is set as 100(%). Also, the Standard Deviation (STD), and the Coefficient of Variation (CV) was calculated as follows;

|  | first | second | third |
|---|---|---|---|
| Sample 1: |  |  |  |
| Mean Value | 100.0 | 94.7 | 164.7 |
| STD | 9.0 | 20.3 | 22.4 |
| CV | 9.0 | 21.4 | 13.6 |
| Sample 3: |  |  |  |
| Mean-Value | 100.0 | 98.8 | 91.2 |
| STD | 9.4 | 12.6 | 11.7 |
| CV | 9.4 | 12.7 | 12.9 |

Figure 9:
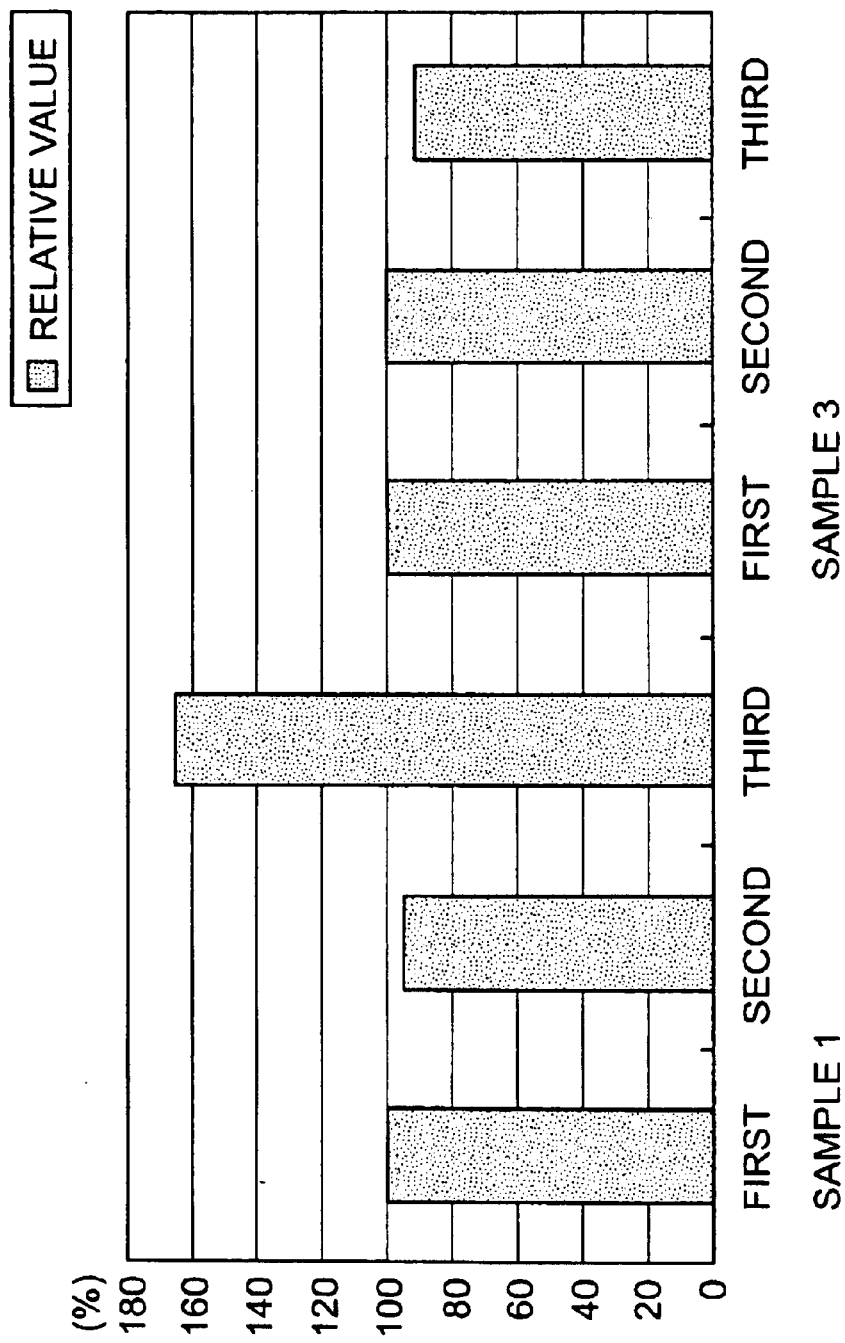
FIG. 9 is a graph which shows the DPV measurement results for Sample 1 and Sample 3.

Regarding Samples 1 and 3, said Mean Values (relative values) of ipa is also shown in FIG. 9.

It was found from the above results that Samples 1 and 3 were especially desirable. In particular, it was found that Sample 3 was most suitable for use a plurality of times.

Furthermore, in all of Samples 1 through 3, since coating is performed using a PTFE resin, the film thickness of the coating can easily be reduced, so that an extremely fine integration of the electrodes can be realized. Furthermore, since coating is performed using a PTFE resin, a complete seal to the base parts (welded parts) on the substrate side of the pin electrodes can easily be obtained.

Example 2
(Evaluation of Uniformity of Effective Surface Area)

As conducted in First Embodiment, the lateral surface portions of the pins were coated with a PEEK resin, and a tabular member of PTFE was applied, thereby Sample 4 was prepared. The pins were covered with the tubular shaped PEEK resin, followed by heat-treatment (heat shrinkage was induced), thereby the coating was performed.

Figure 10:
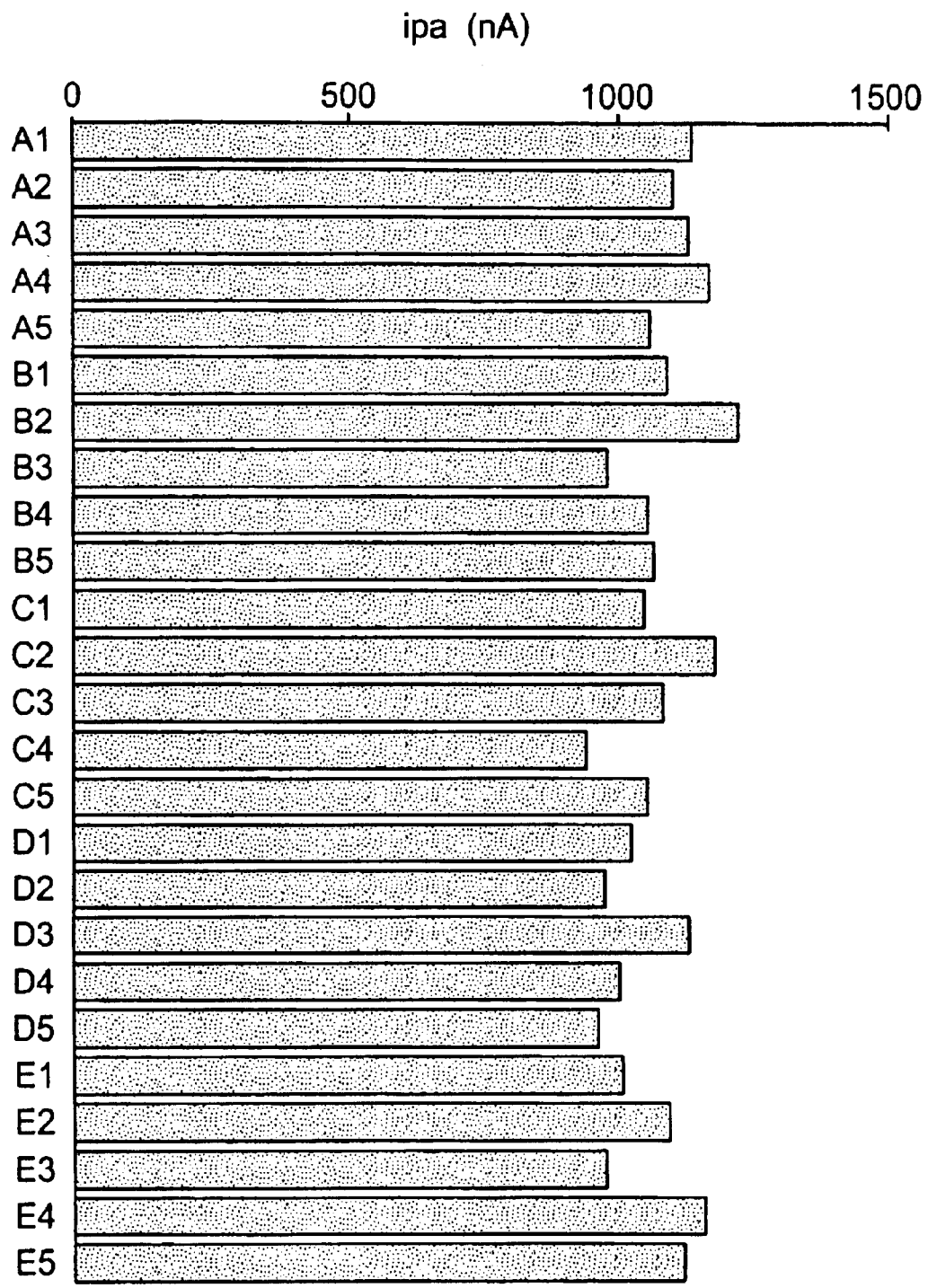
FIG. 10 is a graph which shows the peak current value ipa in the respective pins of Sample 3.
Figure 11:
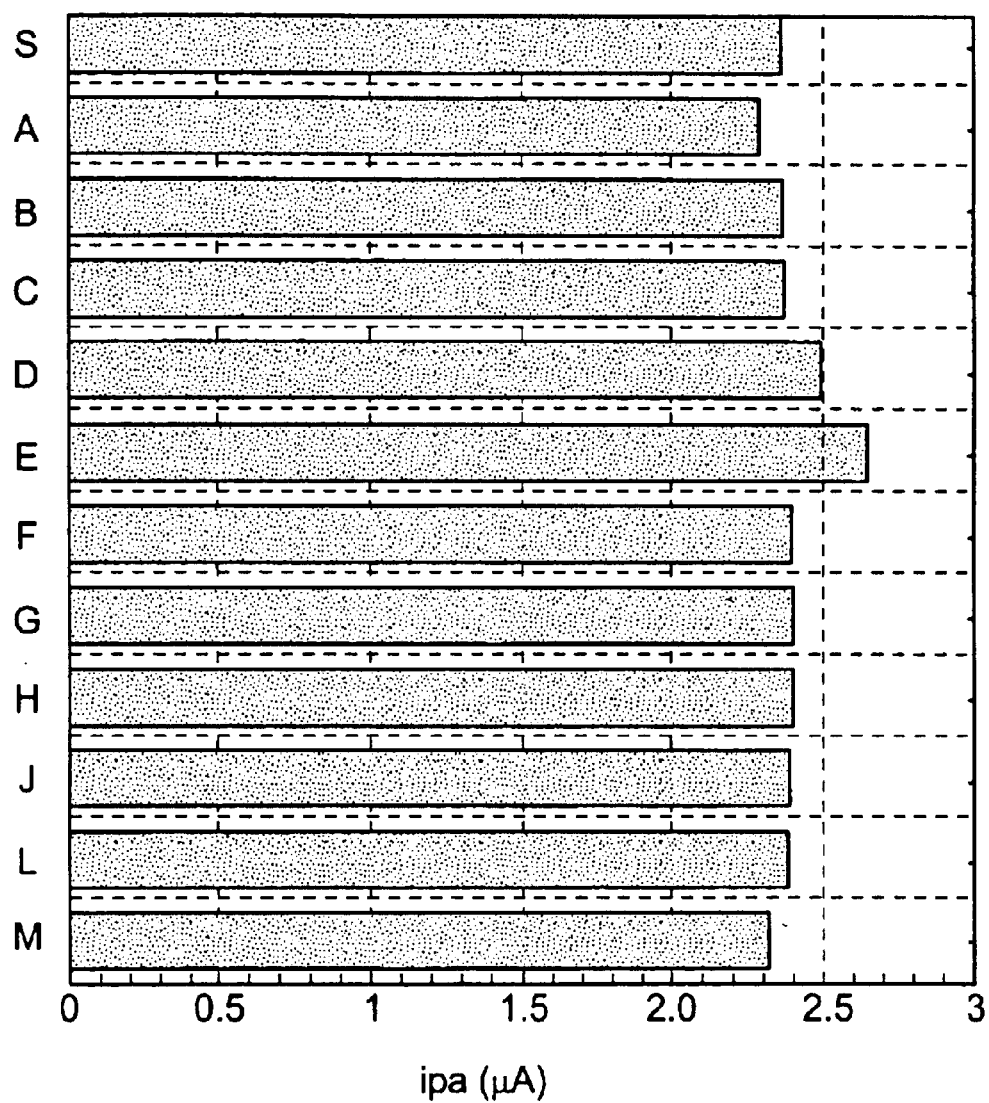
FIG. 11 is a graph which shows the peak current value ipa obtained using an Au electrode manufactured by BAS (control)

Measurements were tried in a 500 μM ferrocenecarboxylic acid system for the Sample in the same manner as described above, and the peak current value ipa, which is proportional to the effective surface area of the electrodes, was determined. The measurement was performed in the same manner as in Example 1. FIG. 10 shows the peak current values ipa measured for the respective pins. A more or less uniform effective surface area was achieved, with a mean value of 1064.1 nA, a standard deviation of 73.6 nA, and a variation coefficient of 6.9%. Thus, it may be seen that the lateral surface portions of the pins are completely sealed by the resin. Furthermore, no great change in this tendency was seen even after use in six consecutive operations; this indicated that the pretreatment caused no expansion of the resin or deterioration of the Au plating surface.

Figure 12:
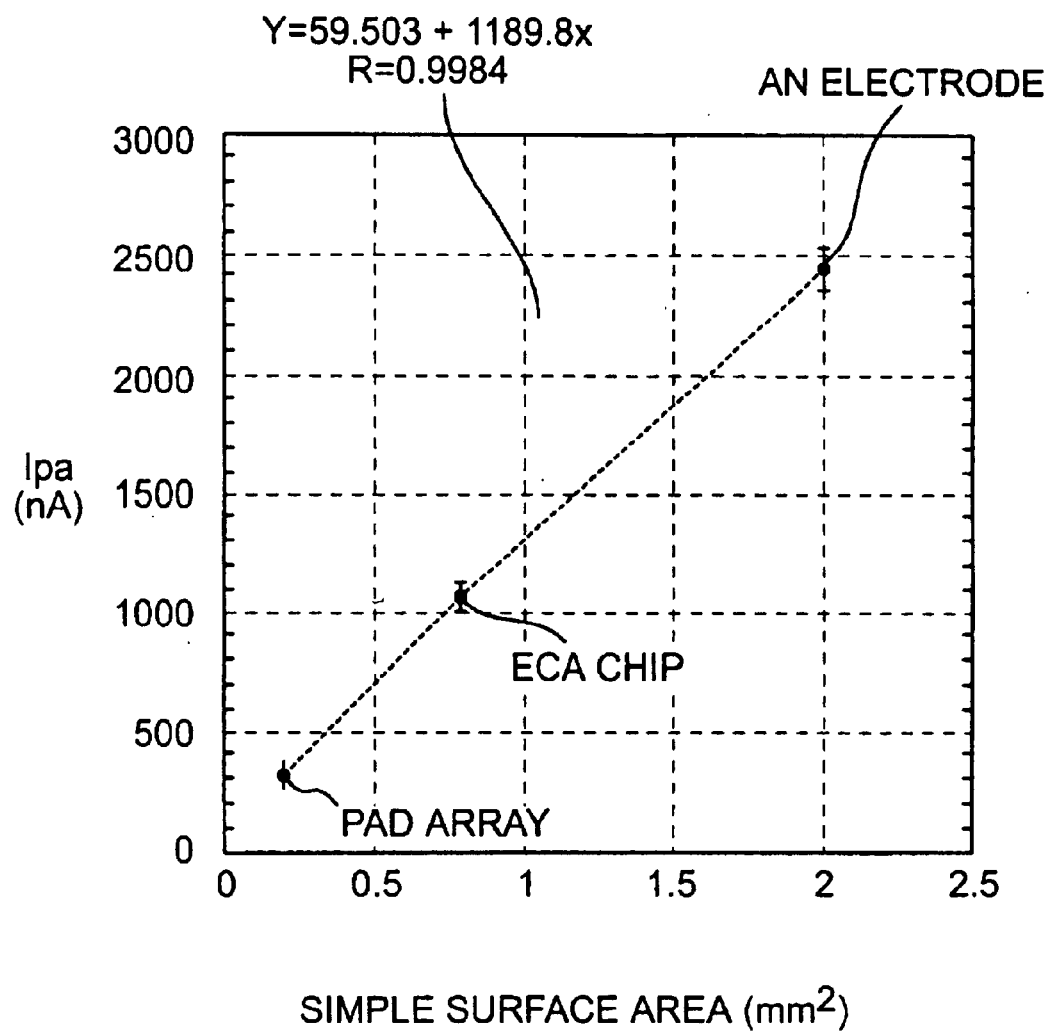
FIG. 12 is a graph which shows the relationship between the simple surface area and ipa.

Furthermore, similar measurements were also tried using a plurality of Au electrodes (effective surface area: 2 mm$^2$) manufactured by BAS. The results obtained are shown in FIG. 12. Since the results obtained, i.e., a mean value of 2.428 μR, a standard deviation of 0.110 PA and a variation coefficient of 4.5%, showed no great difference from the results described above, the uniformity of the effective surface area in Sample 4 was apparent.

Finally, in regard to the relationship between ipa and the simple surface area calculated from the diameter, the results-for a pad array (effective surface area: 0.2 mm$^2$) obtained in the past are also shown in FIG. 12. It is seen that an extremely good correlation is established between the two sets of results. Specifically, these results show that the electrode activity per unit area in Sample 4 is at the same level as that of commercially marketed Au electrodes.

The above-mentioned device makes it easier to reduce to coating film thickness, and easier to form a complete seal as far as the base parts (welded parts) of the pin electrodes on the substrate side.

INDUSTRIAL APPLICABILITY

Configuring the gene detection device and chip pertaining to the present invention in the above-described manner makes it possible to detect genes with greater ease and enhanced sensitivity and throughput. In addition, adapting such a detection chip to a measurement device that allows this chip to be inserted and removed makes it possible to provide a detection system that can analyze genes with greater ease, enhanced sensitivity, and a higher throughput.

The high-sensitivity and high-throughput detection chip and detection device of the present invention is an efficient means of analyzing the relation between genes and their expression in the biological and medical fields. Genetic screening can also be performed by analyzing drug-metabolizing enzymes, cancer-suppressing genes, and other specific genes with the aid of the inventive detection/analysis device for determining gene base sequences, single base substitution SNPs, multiple base substitutions, point mutations, translocations, defects, amplifications, and triplet repeats.

For example, the detection device pertaining to the present invention can perform high-sensitivity, high-throughput procedures, making it possible to collect genetic data for Japanese individuals, to identify genes associated with certain illnesses, and to predict/prevent diseases in the future.

Genetic screening can be useful for selecting the right treatment or picking drugs with minimal side effects.

In addition, results from the genetic analysis of a disease can be used to develop drugs without performing repeated clinical trials or the like.

What is claimed is:

1. A gene detection device comprising:
    a plurality of pins that constitute electrodes; and
    a common electrode that constitutes a counter electrode for said pins and
    a tabular member comprising a plurality of pin holes into which said plurality of pins are respectively inserted;
    wherein at least portions of surfaces of said pins are coated with a first resin, said tabular member is made from a second resin, and said coated portions of said pins are contacted by said tabular member.

2. The gene detection device according to claim 1, wherein said pins contact a surface of a supporting member or are implanted in the surface of said supporting member, and portions of the surface of said supporting member that are not contacted by said pins or in which said pins are not implanted are coated with a third resin.

3. The gene detection device according to claim 2, wherein said supporting member comprises a ceramic.

4. The gene detection device according to claim 3, wherein said supporting member comprises alumina.

5. The gene detection device according to claim 1 wherein the first resin is selected from the group consisting of poly(ether ether ketone), a thermoplasic resin and an epoxy resin, and the second resin is selected from the group consisting of a thermoplasic resin and a flouroresin.

6. The gene detection device according to claim 1, wherein a hole diameters of said pin holes become smaller in a tapered configuration in the direction of insertion of the pins, and the pins are held in the portions of said pin holes where the hole diameter is smallest.

7. The gene detection device according to claim 2, wherein the third resin is a fluororesin.

8. A gene detection device comprising:
a plurality of pins that constitute electrodes; and
a common electrode that constitutes a counter electrode;
wherein said pins have an Au film formed on the surface of an alloy whose main components are Fe, Ni, and Co, and at least portions of surfaces of said pins are coated with a resin.

9. The gene detection device according to claim 8, further comprising a supporting member, wherein said supporting member comprises a ceramic and wherein said pins contact a surface of said supporting member or are implanted in portions of the surface of said supporting member.

10. The gene detection device according to claim 9, wherein said supporting member comprises alumina.

11. The gene detection device according to claim 8, wherein the resin is selected from the group consisting of poly(ether ether ketone), a thermoplastic resin and an epoxy resin.

12. A gene detection chip comprising
a plurality of pins that constitute measurement electrodes; and
a tabular member made from a first resin and having a plurality of pin holes into which said plurality of pins is respectively inserted,
wherein at least portions of the surfaces of said pins are coated with a second resin and portions of the surfaces of said pins are contacted by said tabular member.

13. The gene detection chip according to claim 12, further comprising a common electrode that constitutes a counter electrode for said plurality of pins.

14. The gene detection chip according to claim 12, wherein said pins contact a surface of a supporting member or are implanted in the surface of said supporting member, and lateral surfaces of said pins and portions of the surface of said supporting member that are not contacted by said pins or in which said pins are not implanted are respectively coated with a third resin.

15. The gene detection chip according to claim 14, wherein the third resin is a fluororesin.

16. A gene detection device comprising the gene detection chip according to claim 12, and a measuring device which allows insertion and removal of said detection chip.

17. The gene detection chip according to claim 12, wherein the second resin is selected from the group consisting of poly(ether ether ketone), a thermoplastic resin and an epoxy resin.

18. A gene detection chip comprising:
a plurality of pins that constitute measurement electrodes;
wherein at least portions of surfaces of said pins are coated with a first resin and said pins have an Au film formed on a surface of an alloy whose main components are Fe, Ni and Co.

19. The gene detection chip according to claim 18, further comprising a common electrode that constitutes a counter electrode for said plurality of pins.

20. The gene detection chip according to claim 18, wherein said pins contact a surface of a supporting member or are implanted in the surface of said supporting member, and lateral surfaces of said pins and portions of the surface of said supporting member that are not contacted by said pins or in which said pins are not implanted are respectively coated with a second resin.

21. The gene detection chip according to claim 20, wherein the second resin is a fluororesin.

22. The gene detection chip according to claim 18, wherein the first resin is selected from the group consisting of poly(ether ether ketone), a thermoplastic resin and an epoxy resin.

23. A gene detection chip comprising:
a plurality of pins that constitute measurement electrodes; and
a common electrode that constitutes a counter electrode for said pins; wherein
said pins have an Au film formed on the surface of an alloy whose main components are Fe, Ni and Co.

24. The gene detection chip according to claim 23, wherein said pins contact the surface of the supporting member or are implanted in the surface of the supporting member, and said supporting member is constructed with a ceramic as the main component.

25. The gene detection chip according to claim 24, wherein said pins contact the surface of the supporting member or are implanted in the surface of the supporting member, and said supporting member is constructed with alumina as the main component.

* * * * *

UNITED STATES PATENT AND TRADEMARK OFFICE
CERTIFICATE OF CORRECTION

PATENT NO. : 6,749,731 B2
DATED : June 15, 2004
INVENTOR(S) : Shinichi Kobori et al.

It is certified that error appears in the above-identified patent and that said Letters Patent is hereby corrected as shown below:

<u>Title page</u>,
Item [75], Inventors, please revise "Shinichi Kobori, Tokyo (JP); Kazuhiro Nakama, Nagoshima (JP); Shingo Satoh, Nagoshima (JP); Hiroyoshi Miyhara, Chiba (JP)" to read as follows:
-- Shinichi Kobori, Tokyo (JP); Kazuhiro Nakama, Kagoshima (JP); Shingo Satoh, Kagoshima (JP); Hiroyoshi Miyahara, Chiba-shi (JP) --.

Signed and Sealed this

Twenty-second Day of March, 2005

JON W. DUDAS
*Director of the United States Patent and Trademark Office*